United States Patent [19]

Yabrov

[11] Patent Number: 4,460,574

[45] Date of Patent: Jul. 17, 1984

[54] PROPHYLAXIS OR TREATMENT OF INTERFERON-SENSITIVE DISEASES

[76] Inventor: Alexander A. Yabrov, 45 Wiggins St., Princeton, N.J. 08540

[21] Appl. No.: 159,540

[22] Filed: Jun. 16, 1980

[51] Int. Cl.³ ............................................. A61K 45/02
[52] U.S. Cl. ..................................... 424/85; 435/811
[58] Field of Search ...................... 424/85, 88; 439/68, 439/811

[56] References Cited

U.S. PATENT DOCUMENTS 3,560,611  2/1971  Chany et al. ........................... 424/85
3,975,344  8/1976  Schwartz ............................... 424/85
4,216,203  8/1980  Johnston ................................ 424/85

Primary Examiner—Blondel Hazel
Attorney, Agent, or Firm—Vincent P. Pirri; John F. Witherspoon

[57] ABSTRACT

Prophylaxis or treatment of interferon-sensitive diseases in a human is effected by the rectal or urogenital administration to a human of a liquid pharmaceutical composition of native human interferon (Types I and II), said liquid pharmaceutical composition not being clinically appropriate for intravenous or intramuscular injection.

13 Claims, No Drawings

PROPHYLAXIS OR TREATMENT OF INTERFERON-SENSITIVE DISEASES

BACKGROUND OF THE INVENTION

The field of art to which the invention pertains is interferon, to methods of administering interferon to humans, and to articles comprising interferon for use in such methods.

Interferon is used in clinical trials for treatment of various viral diseases and cancers (#1). Interferon can be produced in vivo by mammals and in vitro by tissue cultures in response to the action of a variety of specific inducers, in particular both viral and non-viral inducers.

Though a great deal of research has been done concerning the physical and chemical attributes of interferon, its chemical structure has not been identified as yet with any degree of certainty. What appears to be established is that interferon is a protein, or at least contains protein as a main component and that part of the molecule consists of carbohydrate radicals. At the present time, four types of human interferon have been identified, i.e., Type I which includes leukocyte interferon, fibroblast interferon, and lymphoblastoid interferon, and Type II or immune interferon.

The failure to determine the chemical structure of interferon is due primarily to the lack of any meaningful quantity of pure interferon for purposes of chemical analysis and to the fact that there exists several molecular species of interferon of different molecular weights and different characteristics, and other considerations.

For clinical applications, interferon is usually administered by intramuscular injections as a concentrated liquid pharmaceutical formulation at levels of 1 million units per ml to 3 million units per ml or more daily, for a period of weeks or a few months, depending on the character and course of the disease to be treated (#1-2). Prior to concentration, native human leukocyte interferon activity may be of the order approximating 20,000 units/ml and perhaps lower. Obviously, to administer 1 to 3 million units of such native interferon (interferon obtained prior to exhaustive purification and concentration techniques) would require the intramuscular injection, on a daily basis, of 50 to 150 ml of the native interferon. The need to concentrate interferon to a tolerable and injectable volume of, for example, one milliliter with an activity of one million international units, is thus obvious.

A further demand, is placed on injectable human interferon in that it should be sufficiently purified in order to avoid or alleviate possible side effects in the human to be treated (intramuscular or intravenous) with interferon. It is not surprising, therefore, that proposed federal regulations presently under consideration with respect to the production and testing of interferon intended for investigational use in humans state that interferon preparations to be used in clinical studies will require a specific activity of at least $10^6$ international units per mg protein and that contaminants should be effectively removed from the final product. These requirements correspond to approximately 1000 times the concentration and purification of native preparation. Moreover, intravenous application will demand a tenfold higher purification (#3).

Various factors, among which can be listed the reputed ineffectiveness of purification and concentration techniques as well as the instability of purified interferon, have impeded the production, purification, concentration, and clinical evaluations of interferon. Prolonged storage, elevated temperatures, and chemical and mechanical manipulations such as shaking, repeated freezing and thawing cycles, frothing during filtration, and the like, tend to readily inactivate various types of interferon. The widely-used method of ethanol purification by Kari Cantell provides an average of only 20% to 30% recovery of the activity of leukocyte interferon (4). Concentration, e.g., lyophilization, may also cause up to 50% loss. Purified human fibroblast interferon possesses such instability that its activity levels are not always reliable. Moreover, even the relatively most stable types of interferon appear to become labile once a high degree of purity has been obtained. Purification and/or concentration techniques include precipitation, evaporation, centrifugation, chromatography, adsorption, lyophilization, and the like. Such techniques are expensive, time-consuming, and the yields of purified material obtained thereby are low. It has also been proposed to add extraneous material to protect and/or increase the stability of the interferon after purification which addition (of material) is contrary to the very objective of purification. On the other hand, native interferon, e.g., human leukocyte interferon, was shown to be relatively highly stable (#1). Native human interferon (Type I) having activities approximating about 5000 international units (U) was discarded rather than "purified" by conventional purification-concentration techniques since the end result was a decrease in the original activity of the native interferon.

THE INVENTION

In accordance with the practice of the invention many of the aforesaid disadvantages are substantially lessened or obviated. Moreover, in the practice of the invention native human interferon (Types I and II) having extremely low activities (by-products so to speak) can be employed with efficacious and therapeutic results. It has now been discovered novel methods of administration for prophylaxis and/or treatment of interferon-sensitive diseases which comprises administering to a human, rectally or urogenitally, a therapeutically effective amount of a liquid pharmaceutical composition comprising native human interferon which has an activity of at least about 5000 international units (U) per ml for Type I interferon (fibroblast, leukocyte, lymphoblastoid) or at least about 1000 international units (U) per ml for Type II interferon (immune interferon), and which is not clinically appropriate for intramuscular or intravenous injection.

The upper limit of activity of native human interferon will depend, to a significant degree, on several factors such as the nature of the cells used for interferon production; the nature of the agent used for production stimulation, e.g., different viruses, viral products, bacteria, bacterial products, or synthetic polymers; the actual production method, e.g., temperature, incubation period, pH range, concentration of cells and inducer, etc.; the type of growth medium and its contents; and the like. A suitable upper limit of activity of Type I interferon, on a milliliter basis, is about 200,000 U, and higher, preferably about 100,000 U, and most preferably about 50,000 U. The lower activity limit which is contemplated in the practice of the invention for Type I interferon is about 5000 U, desirably about 10,000 U, and preferably about 20,000 U. With reference to Type II native human interferon (again on a milliliter basis), the lower limit of activity can be about 1000 U and lower, desirably about 2000 U, and preferably about 5000 U; upper limits of activities are about 50,000 U and higher, about 30,000 U (preferred), and about 10,000 U (most preferred). A unit of interferon, as used herein, is the reciprocal of the dilution of an interferon preparation which causes 50% protection against cytopathogenic effect of vesicular stomatitis virus in tissue culture. An adjustment is made against an international standard preparation 69-19 (#5).

As used herein, the term "native human interferon" contemplates a liquid mixture, generally aqueous mixture, comprising cells which have been isolated from humans and which have been stimulated or activated in vitro with an interferon inducer, viral or non-viral, for a period of time sufficient to produce interferon, the resulting stimulated mixture having an activity of at least about 5000 U per ml for Type I interferon or about 1000 U per ml for Type II interferon. This activity is primarily due to the interferon thus induced; however, the mixture may contain other biologically active substances, e.g., lymphokines such as migration inhibitory factor, lymphocyte activating factor, macrophage activating factor, and the like. Cells and/or cell debris may be removed, if desired, by additional preliminary processing techniques such as by centrifugation. With respect to the inducer and depending upon its nature, well known techniques may be employed to inactivate, remove, neutralize, or destroy the inducer, if desired or necessary. By way of illustrations, the inducer may be inactivated by pH adjustment, or removed by chromatographic techniques, or neutralized with specific antibodies, or destroyed enzymatically. Avoidance of undue purification retains biologically active material in the native human interferon. The resulting mixture is a physiological liquid containing native human interferon.

As used herein, the term "not (being) clinically appropriate" contemplates a liquid mixture, generally aqueous mixture, comprising native human interferon which does not meet all of the aforesaid proposed federal regulations. Such liquid mixture possesses an activity level substantially below $10^6$ U per ml, is impractical for intravenous and intramuscular treatments in view of the relatively large volumes which must be injected to attain an activity dosage of $10^6$ U, and is clinically unsuitable for intravenous and intramuscular treatments.

The liquid pharmaceutical compositions may take the form of aqueous or non-aqueous solutions, suspensions and emulsions of native human interferon, with or without other active and/or inactive ingredients. Preferably an aqueous medium of native human interferon is employed since it is readily obtained in this form after, for example, preliminary centrifugation. Diluents, medicaments, and other additives can be incorporated into the liquid pharmaceutical composition, e.g., glycerol, low molecular weight polyethylene glycol, buffering agents, fragrances, stabilizers, antibiotics, nutrients, transfer factor, thyrosin, vitamins, trace elements, glucose, etc.

Native human interferon, preferably fibroblast interferon and leukocyte interferon (Type I and Type II) is employed in the practice of the invention. Native human interferon can be produced by techniques conventional in the art by established induction or activation procedures of human interferon-producing cells in vitro with a known inducer or activator, e.g., viral, non-viral, and chemical. Illustrative inducers or activators include viral, e.g., Sendai virus, bacterial products, e.g., Staphylococcal Endotoxin A; synthetic polymers, e.g., polyI.polyC. Human interferon-producing cells which are well known in the art and which can be induced or activated in vitro include, for example, cells from organs and tissues such as foreskin fibroblasts, peripheral blood leukocytes, and others. In accordance with known procedures, the human interferon-producing cells are suspended in a suitable physiological growth medium, e.g., MEM, Basal Medium Eagle, Medium 199 with Earle's Unmodified Salts, RPMI Medium 1629, 1634 or 1640, and the like (#6). Desirably there is included human agamma serum and an antibiotic(s), e.g., gentamycin, streptomycin, neomycin, and the like. A pH of about 7.3, is desirably maintained; temperature can be about 37.5° C. or lower.

A therapeutically effective amount of the liquid pharmaceutical composition comprising native human interferon is administered rectally or urogenitally desirably at spaced intervals, generally over a period of several days or several weeks, e.g., up to 6 weeks or longer, depending on the nature of treatment (prophylaxis or disease) and other variables such as type and severity of the disease, the total activity of dosage, etc. In general, administration is continued over a period of time until medical tests on the patient establish confirmation with respect to the condition being treated according to the invention. In rectal and urogenital (intravaginally or into the bladder) applications the liquid pharmaceutical composition is introduced via conventional techniques desirably to provide maximal body absorption, e.g., drop-wise.

By the practice of the invention there is afforded an economical method of administering, rectally and/or urogenitally, native human interferon, oftentimes of by-product activity, for prophylaxis and/or treatment of interferon-sensitive diseases, especially viral diseases and tumors such as viral hepatitis, enteritis, prostatitis, prostatocystitis, vulvitis, vaginitis, etc.; carcinomas of rectum, prostate, bladder, etc.; leukemia; and others.

Copending U.S. patent application Ser. No. 075,754 entitled Preactivated Leukocytes by A. A. Yabrov, filed Sept. 14, 1979, describes methods for arresting or causing the regression of growth of tumors or leukemic cells by treatment with activated human leukocytes interferon. The subject matter of that patent application is incorporated by reference into this application.

It is apparent that native human interferon which is contemplated for use in the invention is much less expensive than injectable (intramuscular and intravenous) human interferon. Inasmuch as the native human interferon utilized in the present invention has not been subjected to intensive purification and concentration techniques it has not sustained the relatively large overall losses of activity as is the case with conventionally purified and concentrated human interferon. Additionally, the invention contemplates the use of "by-product" interferon, that is, native human interferon of low activity, e.g., about 5000 U, which is generally discarded as being unsuitable in such techniques. Thus, the practice of the present invention, in effect, makes "additional" interferon available for clinical use since we have obviated the loss and discard factors alluded to above. Once the native human interferon is produced, additives may be incorporated therein, and the resulting liquid pharmaceutical composition bottled, e.g., in disposable glass or plastic bottles of varying volume, e.g., 50 ml to 500 ml, or in disposable containers or articles suitable for enema use generally of small volume, e.g., 10 to 50 ml. The liquid pharmaceutical composition is ready for direct clinical application. Desirably it is maintained at a temperature below room temperature, e.g., about +4° C. It possesses a suitable and useful shelf life, e.g., one month and longer. The bottled or containerized liquid pharmaceutical composition may vary in activity over the ranges indicated previously. If desired, one can also administer, rectally or urogenitally, interferons of high purity and/or concentration.

By the practice of the invention the administration of interferon is maximally simplified. Application by the patient himself is easily performed. Rectal and urogenital application of native human interferon obviates possible side effects which may be caused by relatively high molecular weight proteinaceous contaminants contained therewith since the mucous membrane, e.g., intestinal, vaginal, etc., prevents such contaminants from penetrating into the body. Thus at the region of body administration we have a "natural body filter" which causes a beneficial separation to take place by allowing passage of the active interferon therethrough while blocking passage of the aforesaid contaminants. Fibroblast interferon is known to be less stable in its liquid form than leukocyte interferon or lymphoblastoid interferon. Accordingly, native human fibroblast interferon in particular (but not excluding other native human Type I and Type II interferons) can be converted to a solid form, e.g., tablet, rod, pellet, capsule, etc., especially by lyophilization of the liquid pharmaceutical composition containing the same, thereafter containerized, stored, and when ready for use it can be dissolved in measured quantities of water and administered rectally and/or urogenitally in accordance with the present invention. Alternatively, the native interferon in the form of, for example, slow release polymeric media, slow release devices, and other similar type may also be administered rectally or urogenitally.

Thus, in various embodiments the invention contemplates multi-package systems especially two-package systems of usable shelf life (generally at least one month), one package containing a pharmaceutical composition of native human interferon in solid form, the other package containing a measured amount of liquid, essentially water, with/without additives illustrated previously, in a suitable container (disposable preferred) as illustrated above. Mixing measured amounts of the contents of the two packages to obtain a solution, suspension or emulsion of desired activity is readily accomplished by the clinician or even the patient himself by following the appropriate directions prescribed by the manufacturer and/or doctor.

Unless otherwise noted to the contrary, all percentages represent percent by weight. The following Examples are illustrative.

EXAMPLE 1

Preparation of Human Leukocyte Interferon (Type I)

A. Buffy coats obtained from healthy human donors are pooled. Cold solution of 0.8% $NH_4Cl$ is added (the ratio of buffy coats and $NH_4Cl$ solution being 1:10). After 10 minutes incubation at 4° C. the resulting suspension is centrifuged at 1000 rpm for 10 minutes. The supernatant is discarded. The pellet (sediment) is resuspended in cold 0.8% $NH_4Cl$ solution and after 10 minutes incubation recentrifuged as described above. After the second $NH_4Cl$ treatment the leukocytes are suspended in MEM medium containing 4% agamma human serum, 25 microgram per ml of neomycin, and 100 units of native human leukocyte Type I interferon, the concentration of leukocytes in the suspension being adjusted to $10^7$ cells per ml. This suspension is maintained in a water bath (about 37.5° C.) with gentle continuous stirring by a magnetic stirrer. After two hours, the inducer, virus sendai (150 hemagglutination units per ml), is added to the stirred suspension. Native human interferon is collected in about 20 hours. The cells and cell debris are removed by centrifugation (2500 rpm for 10 minutes). Virus sendai is neutralized within a four to five day period at pH 2.2 at 4° C. after which the pH is adjusted to 7.3. The resulting liquid contains native human leukocyte interferon (Type I). Other methods of production of interferon are well documented in the art (#1).

B. The native human interferon thus derived is assayed for its antiviral potential. This is performed by serial 2-fold dilution of the native interferon (e.g., from 1:100 to 1:100,000) in a tissue culture microplate in a volume of 0.05 ml per well. A tissue culture suspension of human cells (Hep-2) is added to each well ($10^5$ cells per ml; 0.1 ml of the suspension per well). The microplates are incubated for 24 hours at 37° C.; then vesicular stomatitis virus is added (100 cytopathogenic doses in 0.1 ml per well), and the plates are kept at 37° C. for another 48 hours. A total of 72 hours after the beginning of the assay the microplates are treated with a solution containing 0.5% crystal violet, 3.3% formalin (37% solution of formaldehyde), 33.3% ethanol, 0.16% NaCl, and 66.7% distilled water in order to fix the cells not destroyed by the cytopathogenic effect of the virus. The wells containing cell monolayer protected by interferon against the viral cytopathogenic effect are easily seen . . . since they are stained with crystal violet absorbed by the cell. The wells in which the native interferon was diluted beyond its protective capacity are not stained since all cells are destroyed by the virus. The reciprocal figure of the final dilution which protects 50% of the cells is considered to be the titer of the native interferon under assay. For example, the native interferon protects 50% of cells being diluted 1:20,000. The titer of this interferon is 20,000 U, per ml (this titer should be adjusted to the standard international unit, which adjustment is not considered in this Example). If two million units of this native interferon is required daily to treat the disease, then 100 ml should be used (20,000 U/ml times 100 ml). The application of treatment can be rectally, e.g., as an enema three times per day using 30-35 milliliters per application; or, it can be applied rectally once a day in a continuous, drop-wise manner using, for example, one ml per minute for a period of about 100 minutes. In the latter mode of treatment, a bottle of native interferon can be placed 1 to 1.5 meters above the bedded patient. The application of treatment can also be urogenitally, e.g., intravaginally or into the bladder. The method of application depends on the character of the disease to be treated and on the dosage of interferon prescribed daily.

EXAMPLE 2

One of the widely-spread diseases, especially among young children, e.g., up to one year old, is viral enteritis. This disease is characterized by a severe course and high mortality. Only symptomatical treatment is available. Conventional antibiotics are not efficient since they do not possess the antiviral activity.

Two groups of patients (10 in each group) matching in the diagnosis (viral enteritis), age (up to one year old), state, and course of the disease, are selected. Patients in Group A (control) are treated by conventional methods (including also vitamins and trace elements, water, salts, and acid-base balances regulation, antibiotics when necessary).

Patients in Group B (experimental) in common with the above conventional treatment are also treated rectally with the aqueous pharmaceutical composition containing native human leukocyte (Type I) interferon of Example 1 in a continuous dropwise fashion—dosage per day being one million units per kilogram body weight until marked improvement in the course of the disease is recorded, generally within a period of approximately 7–10 days or slightly longer.

There results a statistically significant improvement in the course of the disease of the experimental Group B patients as compared with the course of the disease of the patients of Group A (control). Improvement in the course of recovery of the patients in Group B exceeds by a factor of more than 200% the course of recovery of the patients in Group A.

EXAMPLE 3

Preparation of Native Human Fibroblast Interferon (Type I)

Human diploid fibroblasts (foreskin fibroblasts, strain FSU, twentieth passage) is used as the source for production of native fibroblast interferon. Fibroblasts (FSU) grown as a monolayer on superbead microcarriers by Flow Laboratories can be used. The microcarrier (0.5g) and the fibroblasts ($3 \times 10^6$ cells per ml) are suspended in a 100 ml of complete growth medium (see Example 1) in 250 ml spinner flask. The suspension is maintained by magnetic spinner (60 to 90 rpm) at about 37° C. in a $CO_2$ incubator. Forty-eight hours later fresh medium containing 200 microgram/ml of polyI.polyC (inducer) is added. After one hour at 37° C. the medium with inducer is reacted, the cells are washed twice with Hanks solution and Eagle's MEM containing 10 microgram/ml of cycloheximide, and three percent human serum is added thereto. After 3.5 hours incubation at 37° C., 3 microgram/ml of actinomycin D is added to the culture. Thirty minutes later the medium with antimetabolites is removed, the cells are washed five times with Hanks solution, and are replaced with fresh medium without serum. After 10 hours the supernatant is harvested and it is centrifuged at 2500 rpm for 10 minutes. The liquid thus derived is used as native fibroblast interferon Type I.

The methods of assay, of application and of activity are similar to those described in the Example 1 for human leukocyte interferon (Type I).

EXAMPLE 4

As an example for "clinical assay of the efficacy of the systemic treatment" by liquid interferon, viral hepatitis can be selected. This viral disease is one of the most common in the world. Among the viruses known to cause it are hepatitis viruses A, B, and, also, non-A/non-B virus. The disease may have a chronic or an acute course. Some patients can also be carriers, not showing symptoms of a current disease.

Two groups of patients (10 in each group) with acute hepatitis are selected, matching in basic features—sex, age, etiology, state and course of the disease. Group A (control) is subjected to a conventional treatment (rest, appropriate diet as tolerated, vitamins and trace elements, glucose, methionine, etc.). Patients in Group B (experimental) in common with the conventional treatment, are also treated rectally with the aqueous pharmaceutical composition comprising native human fibroblast interferon of Example 3 in a continuous, drop-wise fashion—dosage per day being two million units.

Within one to three weeks, at least twice the number of patients from Group B (experimental) as compared with the control patients (Group A) show an obvious improvement in the course of the disease. This improvement is reflected both by the results of physical observations and by appropriate analysis (blood, serum enzymes, pigments in serum, urine and stool). With absence of mortality in severe cases (Group B), the application of treatment utilizing the liquid pharmaceutical composition of native human fibroblast interferon (Type I) of Example 3 is considered to be essential.

EXAMPLE 5

Leukemia is a widely spread disease among humans of various ages. Leukemia can be treated only systemically, i.e., interferon should be absorbed by the body from the place of its introduction into the patient.

Two groups (A and B) of patients with acute leukemia (5 in each group) matched in age, diagnosis, state and course of the disease are selected.

The patients in Group B (experimental) are subjected to 14 days treatment with the liquid interferon composition of Example 1 (rectally, 3 million units daily). After this period of time, treatment with interferon is substituted by conventional chemotherapy (varies with the kind and stage of leukemia). Use of steroids are avoided since they are shown to antagonize the efficacious effect of interferon. The patients in Group A (control) are treated with chemotherapy only.

The patients in Group B (experimental), after remission is achieved, are given preventive courses of interferon every six months, i.e., 3 million units daily for 7 to 10 days.

Statistically significant results with Group B patients (experimental) are obtained in that remission occurs in a shorter period (less than one-half) and in that prolongation of the time of such remission is greater by a factor of more than 100% as compared with the Group A patients (control).

EXAMPLE 6

It is well known that most of cancers can be operated, and the tumor removed, when diagnosed in operable stage. However, in many cases the disease comes back. Relapse is the main danger of operable cancer. In order to avoid it, the patients are subjected to radio-or chemotherapy before or after the operation.

Within the scope of the invention is included the administration of native interferon such as interferon of Examples 1 and 3 as a rectal treatment for every cancer patient subjected to operation. One to three weeks prior to the operation and one to three weeks after the operation one to five million units per day are administered rectally to the patients. The rectal treatments can then be repeated prophylactically for a period of one week every six months for five years.

A decrease in relapses on at least 25% as compared with the average rate based on contemporary statistics shows efficacy of treatment with native interferon contemplated herein.

LIST OF CITATIONS

1. Yabrov, A., textbook entitled *Interferon and Nonspecific Resistance*, Human Sciences Press, New York, N.Y. (1980).
2. Pazin, G. et al., "Prevention of Reactivated Herpes Simplex Infection by Human Leukocyte Interferon after Operation on the Trigeminal Root," *The New England Journal of Medicine*, Vol. 301, pages 225–230, Aug. 2, 1979.
3. FDA Points to be Considered in the Production and Testing of Interferon Intended for Investigational Use in Humans (DRAFT)—April 1980—based on materials at a Workshop on "Human Interferon in the Clinic: Guidelines for Testing" held at the National Institutes of Health (National Cancer Institute), Bethesda, Md., on Oct. 29, 1979.
4. Erickson, J. et al., "Purification of Acid Ethanol-Extracted Human Lymphoid Interferons by Blue Sepharose Chromatography, " *Analytical Biochemistry*, Vol. 98, pages 214–218 (1979).
5. "Interferon Standards: A Memorandum," *Journal of Biological Standardization*, Vol. 7, 000—000, pages 1, 222, 333, 444, 555, 777, 888, 999, 010, 111, 012, 013, (1979).
6. Catalogue on Tissue Culture Products, Grand Island Biological Company (GIBCO), 3175 Staley Road, Grand Island, N.Y. 10472, pages 14, 16, 18 et seq.

What is claimed is:

1. In a method of administration for prophylaxis or treatment of interferon-sensitive diseases in a human with human interferon, the improvement which comprises the rectal or urogenital administration of a therapeutically effective amount of a liquid pharmaceutical composition comprising native human interferon which has an activity of at least about 5000 international units per ml for Type I interferon or at least about 1000 international units per ml for Type II interferon, said liquid pharmaceutical composition not being clinically appropriate for intramuscular or intravenous injection.

2. The method of claim 1 wherein the liquid pharmaceutical composition comprises native human interferon Type I which has an activity of at least about 10,000 international units per milliliter.

3. The method of claim 1 wherein the liquid pharmaceutical composition comprises native human interferon Type II which has an activity of at least about 2,000 international units per milliliter.

4. The method of claim 1 wherein said liquid pharmaceutical composition is administered rectally to the human.

5. The method of claim 1 wherein said liquid pharmaceutical composition is administered urogenitally to the human.

6. The method of claim 2 wherein said native human interferon is human fibroblast interferon.

7. The method of claim 2 wherein said native human interferon is human leukocyte interferon.

8. The method of claims 6 or 7 wherein the liquid pharmaceutical composition comprising native human interferon (Type I) has an activity in the range of from about 20,000 to about 100,000 international units per milliliter and wherein the liquid pharmaceutical composition comprising native human interferon (Type II) has an activity in the range of from about 2,000 to about 10,000 international units per milliliter.

9. A multi-package system comprising, as a first package, native human interferon in solid form, and as a second package, a liquid comprising water, said native human interferon and said liquid upon mixing being capable of forming an aqueous pharmaceutical composition having an activity of at least about 5000 international units per ml for Type I interferon or at least about 1000 international units per ml for Type II interferon, said aqueous pharmaceutical composition being suitable for rectal or urogenital administration to a human but not being clinically appropriate for intramuscular or intravenous injection in such human.

10. The system of claim 9 wherein said aqueous pharmaceutical composition comprises native human interferon Type I which has an activity of at least about 10,000 international units per milliliter.

11. The system of claim 9 wherein said aqueous pharmaceutical composition comprises native human interferon Type II which has an activity of at least about 2,000 international units per milliliter.

12. The system of claim 10 wherein said native human interferon is human fibroblast interferon.

13. The system of claim 10 wherein said native human interferon is human leukocyte interferon.

* * * * *

UNITED STATES PATENT AND TRADEMARK OFFICE
CERTIFICATE OF CORRECTION

PATENT NO. : 4,460,574
DATED : July 17, 1984
INVENTOR(S) : Yabrov

It is certified that error appears in the above-identified patent and that said Letters Patent is hereby corrected as shown below:

On the cover page, the following should be included among the "References Cited":

-- OTHER PUBLICATIONS

Sikora, K., British Medical Journal, Vol. 281, pp. 855-858, 1980. --

On the cover page, the following should be added to the list of U.S. patent documents:

-- 3,773,924    11/1973    Ho et al.    424/85 --

At column 1, line 49, delete the comma.

At column 3, line 10, "69-19" should read -- 69/19 --.

Signed and Sealed this

Twenty-fifth Day of December 1984

[SEAL]

Attest:

GERALD J. MOSSINGHOFF

Attesting Officer

Commissioner of Patents and Trademarks